US009877871B2

(12) United States Patent
Inamoto et al.

(10) Patent No.: US 9,877,871 B2
(45) Date of Patent: Jan. 30, 2018

(54) METHOD FOR USING HYDROGEL SHEET FOR TREATING WOUND (75) Inventors: Yukiko Inamoto, Higashikagawa (JP); Takashi Kamakura, Higashikagawa (JP); Makoto Takahashi, Sapporo (JP); Takehiko Ohura, Sapporo (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 350 days.

(21) Appl. No.: 13/823,220

(22) PCT Filed: Sep. 8, 2011

(86) PCT No.: PCT/JP2011/070461
§ 371 (c)(1),
(2), (4) Date: Apr. 22, 2013

(87) PCT Pub. No.: WO2012/036064
PCT Pub. Date: Mar. 22, 2012

(65) Prior Publication Data
US 2013/0211309 A1 Aug. 15, 2013

(30) Foreign Application Priority Data
Sep. 17, 2010 (JP) ................................. 2010-208928

(51) Int. Cl.
*A61L 15/28* (2006.01)
*A61F 13/00* (2006.01)
(Continued)

(52) U.S. Cl.
CPC ........ *A61F 13/00017* (2013.01); *A61L 15/26* (2013.01); *A61L 15/46* (2013.01); *A61L 15/60* (2013.01)

(58) Field of Classification Search
CPC .... A61F 13/00; A61F 13/00089; A61F 13/02; A61F 13/023; A61F 13/0243; A61F 13/00017; A61L 15/60; A61L 15/26
(Continued)

(56) References Cited

U.S. PATENT DOCUMENTS

| 4,415,628 A | 11/1983 | Cioca et al. |
| 5,693,624 A | 12/1997 | Hardy et al. |

(Continued)

FOREIGN PATENT DOCUMENTS

| EP | 1 051 982 | 11/2000 |
| JP | 58-87153 | 5/1983 |

(Continued)

OTHER PUBLICATIONS

Office Action dated Dec. 16, 2013 in Australian Application No. 2011304133.
(Continued)

*Primary Examiner* — Ophelia A Hawthorne
(74) *Attorney, Agent, or Firm* — Wenderoth, Lind & Ponack, L.L.P.

(57) ABSTRACT

Wound bed preparation in a skin wound area can be carried out by using a hydrogel sheet, wherein the hydrogel sheet is prepared by spreading a hydrogel containing a water-soluble polymer, glycerin, and water on a two-layered laminated film consisting of a polyurethane film and a hydrophobic fiber and the moisture permeability of the hydrogel sheet is 200-2000 ($g/m^2/24$ h).

14 Claims, 9 Drawing Sheets

(51) Int. Cl.
 *A61L 15/26* (2006.01)
 *A61L 15/60* (2006.01)
 *A61L 15/46* (2006.01)

(58) Field of Classification Search
 USPC ....... 602/41–44, 46, 48, 52, 54, 58; 524/916
 See application file for complete search history.

(56) References Cited

U.S. PATENT DOCUMENTS

| | | | |
|---|---|---|---|
| 5,846,214 | A | 12/1998 | Makuuchi et al. |
| 2009/0187130 | A1* | 7/2009 | Asmus .................... A61L 15/46 |
| | | | 602/57 |
| 2010/0209411 | A1* | 8/2010 | Pellico ................. A61K 9/0046 |
| | | | 424/94.2 |
| 2010/0324464 | A1* | 12/2010 | Kamakura .............. A61L 15/16 |
| | | | 602/43 |
| 2013/0171224 | A1* | 7/2013 | Percival ................. A01N 59/26 |
| | | | 424/404 |

FOREIGN PATENT DOCUMENTS

| | | |
|---|---|---|
| JP | 4-272765 | 9/1992 |
| JP | 8-187280 | 7/1996 |
| JP | 2006-61263 | 3/2006 |
| WO | 01/15750 | 3/2001 |
| WO | 2005/037336 | 4/2005 |
| WO | 2007/007115 | 1/2007 |
| WO | 2009/019485 | 2/2009 |
| WO | 2009/107189 | 9/2009 |

OTHER PUBLICATIONS

Martineau et al., "Evaluation of a bi-layer wound dressing for burn care II. In vitro and in vivo bactericidal properties", Burns, vol. 32, 2006, pp. 172-179.

International Preliminary Report on Patentability and Written Opinion dated Apr. 16, 2013 in International (PCT) Application No. PCT/JP2011/070461.

International Search Report dated Oct. 18, 2011 in International (PCT) Application No. PCT/JP2011/070461.

H. Oka, "Recent Understanding of Bedsore Evidence, Treatment Evidence, Wound Healing Theory—Wound Bed Preparation and Moist Wound Healing", EBM Journal, 2007, vol. 8, No. 5, pp. 682-686, with partial English translation.

N. Oura, "New Findings of Wound Management I, What Is Wound Bed Preparation?", Japanese Journal of Plastic Surgery, 2007, vol. 50, No. 5, pp. 533-541.

H. Ojimi, "New Wound Management, Recent Transition of Wound Management—from Infection Prevention to Rapidly, Gently, Beautifully", Japanese Journal of Pediatric Surgery, 2006, vol. 38, No. 4, pp. 427-432.

K. Matsuzaki, "Wound Bed Preparation—Wound Healing for Understanding TIME", Nippon Sosho/Ostomy/Shikkin Care Kenkyu (J. Jpn. WOCN), 2006, vol. 10, No. 2, pp. 6-13, with partial English translation.

Y. Qin, "Textile materials for wound care", Textile Asia, 1997, vol. 28, No. 4, pp. 37-38.

* cited by examiner

METHOD FOR USING HYDROGEL SHEET FOR TREATING WOUND

TECHNICAL FIELD

The present invention relates to a hydrogel sheet for a wound and a method for using the sheet, wherein the sheet, in a skin wound area which is accompanied with an infection, or if not accompanied with an infection, is in a marginal carrier state considered to be a boundary state between an infection and a bacterial colonization, has an activity for removing a biofilm formed by bacteria, an activity for removing bacteria from an infected wound and/or an activity for suppressing a bacterial growth in a wounded area in which an infection is predicted, prevents a maceration of a healthy skin including the wound margin or an infection by bacteria etc. by, for example, absorbing an exudate etc., as well as achieves an excellent moisture control in the wound area to carry out wound bed preparation, and further is excellent in followability and stretchability, has a self-adhesiveness, and can avoid a pain or a recurrent damage in a regenerated skin at the time of exchange.

Also, the present invention relates to a method for treating a wound which is useful for improving a wound healing environment by carrying out wound bed preparation by applying said hydrogel sheet for a wound to an affected area such as a wound etc. to remove an inactive tissue, a crust or a biofilm etc., suppress an infection, adjust a wound bed environment, and the like.

Wound bed preparation means adjusting an environment of a wound surface to promote a wound healing, specifically, carrying out removal of a necrotic tissue, reduction of a bacterial load, prevention of dryness in a wounded area, control of an excessive exudate or management of a wound margin.

BACKGROUND ART

Generally, a wound healing process progresses from "(1) bleed-coagulating phase", to "(2) inflammatory phase", "(3) growth phase", and "(4) mature phase", and in "(1) bleed-coagulating phase", bleeding is stopped by a coagulation factor or a platelet, and a growth factor or a cytokine such as a platelet-derived growth factor is released from a platelet. Subsequently, in "(2) inflammatory phase", these factors cause an inflammatory cell infiltrate such as a neutrophil or a macrophage, then a necrotic tissue is phagocytized, and a wound is cleaned. Concurrently, further chain-reaction releases of a growth factor or a cytokine such as transforming growth factor-β (TGF-β) or fibroblast growth factor (FGF) from these cells are observed. Also, proteases such as matrix metalloproteinase (MMP) are released due to the melting of necrotic tissue proteins. As the wound is cleaned, the phase shifts to "(3) growth phase". The factors released in the phase (2) promote a migration and a growth of a fibroblast or a keratinocyte etc. Extracellular matrices as represented by collagen are synthesized from the fibroblast to become a scaffold for a cell migration or adhesion etc. Also, angiogenesis occurs, and a granulation tissue made from a mixture of various cells such as a new blood vessel or a fibroblast and extracellular matrices such as collagen fills the defect in the tissue. Furthermore, a wound area is reduced by two mechanisms, i.e., an epithelialization by a migration of keratinocytes and a wound contraction by myofibroblasts in a wound covered by a good granulation. When a wound is closed in this way, "(4) mature phase" commences and a scar tissue is formed. The scar, which was initially reddish, is matured by mechanisms such as a remodeling of the extracellular matrices over several months to become white and soft. A chronic damage means a damage in which a healing is delayed by a dysfunction of any one of processes (1) to (4). The protracted and chronic "(2) inflammatory phase" can be often regarded as a dysfunction of the transition from (2) to (3). In the molecular and cellular level, mechanisms such as an abnormality of cells, an abnormality of exudates, or an abnormality of extracellular matrices are considered to be compositely involved in such chronic inflammation state. Accordingly, in order to get out of a chronic inflammation and rapidly shift the healing step to "(3) growth phase", it is necessary to adjust the wound surface environment.

In this way, a healing is not achieved without adjusting a wound surface environment, a residue of foreign substances on a skin wound surface causes an inflammation or an infection etc., and a residue of a necrotic tissue causes an accumulation of an exudate below a wound surface, a formation of an abscess, and a difficulty in evaluating the actual wound depth. Accordingly, carrying out a debridement directly leads to a management of an exudate as well as a control of an infection.

The presence of an inactive tissue or an abnormal granulation, a damaged tissue, a biofilm in Critical colonization (the initial state of an inflammation as a body's immune response in which a healing is stopped) and the like are deeply-involved in a delay of a healing. Therefore, it is well known that debriding of a wound, removal of a necrotic tissue, removal of an exudate, removal of an abnormal granulation, removal of a biofilm and the like are important for the healing process of a wound or a skin disease, and a hydrogel or an ointment etc. is used in these therapies, especially in debriding of a wound, removal of a necrotic tissue, removal of an abnormal granulation and the like.

A conventional sheet-like hydrogel (PVA hydrogel etc.) contains a large amount of purified water in the formulation and is used in the hope of autolytic activities such as a maceration of a necrotic tissue etc. However, said hydrogel lacks self-adhesiveness and stretchability, and thus is difficult to be used in a flexure or a flexion. Also, since the water absorbability of said hydrogel is low, an exudate etc. accumulates, leading to a problem of a maceration of a healthy skin including a wound margin (Patent Document 1).

A gel-like hydrogel is useful in therapy, especially in the therapy of a wound with a sinus formation etc., but has problems, for example, in that a surgical debridement may be required in the removal of it in some cases.

As an ointment, a protease-containing formulation [a fradiomycin sulfate.trypsin-containing formulation (francetin), a fradiomycin powder, a trypsin (trypsin powder), a bromelain-containing formulation (bromelain), a streptokinase.streptodornase-containing formulation (varidase) or a fibrinolysin.deoxyribonuclease-containing formulation (Elase, Elase C)] is used in the removal of a necrotic tissue etc. However, such formulation causes a hypersensitivity to the drug, or a contact dermatitis or a maceration in the surrounding skin, and thus has problems, for example, in that the healthy skin in the wound surroundings is needed to be protected by Vaseline etc.

Also, one of the delay factors of a wound healing is considered to be a biofilm formation on an ulcer surface by bacteria. Conventionally, a disinfectant or an antimicrobial agent for external use has been used against the biofilm, but the disinfectant causes a delay of a wound healing due to its cytotoxicity and the antimicrobial agent has a problem of a development of resistant bacteria etc.

Meanwhile, in the removal of a lesion or the softening after a physical therapy (cryotherapy, laser therapy, phototherapy, ultrasound therapy, or excision etc.) or a chemical therapy (a peeling therapy such as salicylic acid, monochloroacetic acid, glutaraldehyde, phenol, or ethanol etc.), in the treatment of a skin cancer having a large amount of exudates or a necrotic tissue etc., or the like, a gauze, a sponge, a hydrocolloid, a polyurethane, a hydrogel, a wadding, an other fibrous material and an ointment are generally used.

Especially, in the treatment of an unresectable breast cancer or maxillary cancer, a skin metastatic cancer, or an other malignant tumor which is exposed on a skin and self-destructed, an administration of an ointment having antimicrobial and antiulcer effects etc. or a covering with a gauze or an other fibrous material etc. has been carried out. However, although a gauze or an other fibrous material absorbs a liquid by a capillary phenomenon, the absorbed blood or exudate become dried and these fibers are immersed in said tissue, and therefore, the tissue is ripped at the removal of the fibrous material and often lead to a bleeding with a great pain.

A conventional hydrogel or a polyurethane film etc. has a problem of its low water absorbability leading to a maceration of an affected area and a surrounding healthy skin.

A hydrocolloid absorbs an exudate by swelling of the hydrophilic colloidal particles contained in the hydrophobic base material, but it becomes out of shape by water absorption and a gel-like material likely to remain on the affected area at the time of exchange. Also, a hydrocolloid is usually translucent to opaque, leading to a difficulty in observing a wound surface. Furthermore, it has a strong adhesive power, thus often causes a pain at the time of exchange, and has a risk of causing an irritation in peeling.

A polyurethane foam absorbs a large amount of exudates, but has a problem of readily causing a maceration and an infection of an affected area and a surrounding skin in the management of a wound having a large amount of exudates.

A self-adhesive polyurethane film, i.e., a wound covering-material in which an acrylic adhesive is spread on a polyurethane film, is very excellent in stretchability, but has no absorbability. Therefore, when said film is applied to a wound surface on which an exudate exudes, a liquid pool develops and thus drainage is required. Also, its adhesive power is strong, and thus has a risk of not only causing a pain, but also damaging a regenerated skin at the time of exchange (Patent Documents 2, 3, and 4).

Although an alginate gel is excellent in hemostatic property and absorbability, it turns into a gel by an exudate, and thus gel-like materials easily remain on a wound surface at the time of exchange. Also, because said gel is an open system, it requires to be covered with a film material etc. to keep moisture, prevent a bacterial invasion, and prevent a bacterial growth (Patent Document 5).

As stated above, a hydrogel sheet for a wound, which has self-adhesiveness, is excellent in stretchability, has an absorbability of an exudate, is excellent in a moisture environment maintenance, has activities such as for softening and removing a necrotic tissue or a crust and removing a biofilm formed by bacteria, and is excellent in adjusting a wound bed environment, has been desired.

PRIOR ART DOCUMENTS

Patent Documents

Patent Document 1: Japanese Patent 3773983
Patent Document 2: Japanese Patent Publication 58-87153 A
Patent Document 3: Japanese Patent Publication 4-272765 A
Patent Document 4: Japanese Patent Publication 2006-61263 A
Patent Document 5: Japanese Patent Publication 8-187280 A

SUMMARY OF THE INVENTION

Problems to be Solved by the Invention

The present invention solves the conventional problems, and provides a hydrogel sheet for a wound and a method for using the sheet, wherein the sheet is excellent in adjusting a wound bed environment such as removing a crust or a necrotic tissue, or a biofilm formed by bacteria, suppressing a bacterial count in a wound area and controlling an exudate, and has no risk of causing a pain or damaging a regenerated skin at the time of exchange.

Means for Solving the Problems

The present inventors have studied earnestly in order to solve the above-mentioned problems, discovered that a hydrogel sheet for a wound, wherein the hydrogel sheet is prepared by spreading a hydrogel containing a water-soluble polymer, glycerin, and water on a two-layered laminated film consisting of a polyurethane film and a hydrophobic fiber and the moisture permeability of the hydrogel sheet is 200-2000 ($g/m^2/24$ h), is excellent in adjusting a wound bed environment such as removing a crust or a necrotic tissue, or a biofilm formed by bacteria and controlling an exudate, and has no risk of causing a pain or damaging a regenerated skin at the time of exchange, and finally completed the present invention.

Namely, the present invention is presented in the following aspects.
(1) A sheet for wound bed preparation in a skin wound area characterized in that a hydrogel sheet is used therein.
(2) The sheet according to the above-mentioned (1), wherein the wound bed preparation is removal of a biofilm formed by bacteria in the skin wound area.
(3) The sheet according to the above-mentioned (1), wherein the wound bed preparation is removal of bacteria from an infected wound and/or removal of bacteria from a wounded area in which an infection is predicted to occur and/or suppression of a bacterial growth.
(4) The sheet according to any one of the above-mentioned (1)-(3), wherein the hydrogel sheet is prepared by spreading a hydrogel containing a water-soluble polymer, glycerin and water on a two-layered laminated film consisting of a polyurethane film and a hydrophobic fiber and the moisture permeability of the hydrogel sheet is 200-2000 ($g/m^2/24$ h).
(5) A method for treating a wound characterized by using a hydrogel sheet to carry out wound bed preparation in a skin wound area.
(6) The method for treating a wound according to the above-mentioned (5) characterized by using the hydrogel sheet to remove a biofilm formed by bacteria in the skin wound area.
(7) The method for treating a wound according to the above-mentioned (5) characterized by using the hydrogel sheet to remove bacteria from an infected wound and/or remove bacteria from a wounded area in which an infection is predicted to occur and/or suppress a bacterial growth.

(8) The method for treating a wound according to any one of the above-mentioned (5)-(7), wherein the hydrogel sheet is prepared by spreading a hydrogel containing a water-soluble polymer, glycerin and water on a two-layered laminated film consisting of a polyurethane film and a hydrophobic fiber and the moisture permeability of the hydrogel sheet is 200-2000 ($g/m^2/24$ h).

(9) A therapeutic agent for a wound characterized in that a hydrogel sheet is used therein to carry out wound bed preparation in a skin wound area.

(10) The therapeutic agent for a wound according to the above-mentioned (9) characterized in that the hydrogel sheet is used therein to remove a biofilm formed by bacteria in the skin wound area.

(11) The therapeutic agent for a wound according to the above-mentioned (9) characterized in that the hydrogel sheet is used therein to remove bacteria from an infected wound and/or remove bacteria from a wounded area in which an infection is predicted to occur and/or suppress a bacterial growth.

(12) The therapeutic agent for a wound according to any one of the above-mentioned (9)-(11), wherein the hydrogel sheet is prepared by spreading a hydrogel containing a water-soluble polymer, glycerin and water on a two-layered laminated film consisting of a polyurethane film and a hydrophobic fiber and the moisture permeability of the hydrogel sheet is 200-2000 ($g/m^2/24$ h).

Effect of the Invention

The hydrogel sheet for a wound of the present invention removes a crust, a necrotic tissue or an abnormal granulation, and absorbs an exudate. Furthermore, said sheet has activities for removing a bacterial biofilm or bacteria on a wound surface, or suppressing a bacterial growth, and adjusts a wound bed environment to promote a wound healing. Meanwhile, said sheet absorbs an exudate, and maintains an appropriate moisture environment as well as prevents a maceration of a healthy skin on the wound margin area. Namely, the principal use of this hydrogel sheet for a wound is mild removal of a crust or a necrotic tissue in a wound having a crust or an necrotic tissue etc., mild removal of bacteria in a bacterial biofilm or an infected wound (antimicrobial activity), prevention of a bacterial growth in an acute wound and drainage of an exudate from a wound surface in a vertical direction to maintain an appropriate moisture environment without causing a maceration of a healthy skin including the wound margin, thereby prevent a damage or an infection and restore the soundness of a wound bed. In this way, the hydrogel sheet for a wound of the present invention makes a wound management such as wound bed preparation easy and can achieve a wound healing. Also, this hydrogel sheet for a wound is useful for a physical therapy against a skin disease etc., removal of a lesion after a chemical therapy treatment, or the like. Said hydrogel sheet for a wound is usually got out of a bag and applied to a wound to debride the wound, remove a necrotic tissue, absorb a wound exudate, inhibit an infection, adjust a wound bed, and promote a healing.

BEST MODE FOR CARRYING OUT THE INVENTION

Hereinafter, the present invention is described more in detail.

The moisture permeability of the hydrogel sheet of the present invention is preferably 200-2000 ($g/m^2/24$ h), and more preferably 500-1500 ($g/m^2/24$ h). The moisture permeability less than 200 ($g/m^2/24$ h) is not preferable because of a risk of causing a skin irritation due to dampness. Also, the moisture permeability greater than 2000 ($g/m^2/24$ h) is not preferable because a wound surface cannot be maintained in an appropriate moisture environment for a long time.

As a polyurethane resin constituting the polyurethane film of the present invention, a commonly-used urethane resin such as ether series or ester series can be used, and not limited to them.

The polyurethane film used in the present invention has a thickness of 5-25 μm and a constant load elongation rate of 5% or more.

A thickness of the polyurethane film less than 5 μm is not preferable because the wound surface cannot be maintained in an appropriate moisture environment due to the insufficient mechanical strength and increased pinhole. On the other hand, a thickness of the polyurethane film greater than 25 μm is also not preferable because the constant load elongation rate becomes less than 5%, then its stretchability is impaired, and a protection of a wound surface becomes difficult, and also because the transparency decreases and an observation of a wound surface becomes impossible.

As a hydrophobic fiber laminated on the polyurethane film, polyester, nylon, acryl, polypropylene, or polyethylene etc. can be used.

The moisture permeability of the two-layered laminated film consisting of the polyurethane film and the hydrophobic fiber prepared in this way is preferably within the range of 200-5000 ($g/m^2/24$ h) so as to maintain an appropriate moisture environment for promoting a healing of a wound surface for a long time, and more preferably 300-3000 ($g/m^2/24$ h). When the moisture permeability is greater than 5000 ($g/m^2/24$ h), a moisture environment cannot be maintained for a long time and its promoting effect on a healing of a wound surface decreases. Also, the moisture permeability less than 200 ($g/m^2/24$ h) is not preferable because of a risk of causing a skin irritation due to dampness.

As the water-soluble polymer, for example, gelatin, hydrolyzed gelatin, polyacrylic acid, sodium polyacrylate, partially neutralized polyacrylate, starch polyacrylate, polyvinyl alcohol, polyvinylpyrrolidone, hydroxypropylcellulose, hydroxypropyl methylcellulose, hydroxyethyl cellulose, methylcellulose, carmellose sodium, carboxy vinyl polymer, methoxyethylene-maleic anhydride copolymer, N-vinyl acetamide copolymer, xanthane gum, or gum acacia etc. can be used alone or in a combination of two or more of them, and the combination of polyacrylic acid, partially neutralized polyacrylate and carmellose sodium is especially preferred.

The amount of the above-mentioned water-soluble polymer in the hydrogel sheet is 3-20% by weight per gel weight, and more preferably 5-15% by weight. The amount less than 3% by weight is not preferable because the gel viscosity becomes too low leading to a difficulty in forming a patch. The amount greater than 20% by weight is also not preferable because the water-soluble polymer is not homogeneously dissolved in the gel and a good gel cannot be formed.

The amount of water in the hydrogel sheet is 30-80% by weight per gel weight, and preferably 40-75% by weight. The water content greater than 80% by weight is not preferable because the exudate absorbability decreases. Also, the water content less than 30% by weight is not preferable because the adhesive power becomes too strong leading to a risk of causing a pain or damaging a regenerated skin at the exchange of the wound covering-material, and because the moisture retention effect on the skin decreases and an appropriate moisture environment for promoting a healing of the wound surface cannot be maintained.

Also, the amount of glycerin in the hydrogel sheet is 10-40% by weight per gel weight, and preferably 15-30% by weight. When the amount of glycerin in the hydrogel sheet is less than 10% by weight, the moisture retention effect on a skin decreases and an appropriate moisture environment for promoting a healing of a wound surface cannot be maintained. Also, when the amount of glycerin in the hydrogel sheet is greater than 40% by weight, a portion of glycerin which cannot be retained floats into the gel surface, causing problems such as stickiness at the time of application and decrease in adhesive power.

The components constituting the hydrogel sheet other than the above-mentioned components are not especially limited, and, for example, excipients, moisturizers, stabilizing agents, or cross-linking agents etc. can be contained.

As the excipients, for example, kaolin, titanium oxide, anhydrous silicic acid, zinc oxide, or bentonite etc. can be used alone or in a combination of two or more of them. However, since it is necessary for the hydrogel sheet to have a transparency so that a wound surface can be observed when the hydrogel sheet is applied to the wound surface, anhydrous silicic acid is especially preferred, and the amount is preferably 0.1-5% by weight per gel weight.

As moisturizers other than glycerin, for example, D-sorbitol solution, 1,3-butylene glycol, dipropylene glycol, polyethylene glycol, polypropylene glycol, or DL-sodium pyrrolidone carboxylate solution etc. can be used alone or in a combination of two or more of them, and the amount is preferably 10-30% by weight per gel weight.

As the stabilizing agents, for example, edetate, p-hydroxybenzoate ester, tartaric acid, tocopherol acetate, ascorbic acid, or sodium bisulfite etc. can be used alone or in a combination of two or more of them. Also, the pH of the hydrogel sheet is preferably within the range of pH 3.5-6.5 in light of the skin irritation, and more preferably within the range of pH 4.0-5.5.

As the cross-linking agents, for example, a polyvalent metal compound etc. such as dried aluminum hydroxide gel, aluminum glycinate, dihydroxyaluminum aminoacetate, synthetic hydrotalcite, or aluminometasilicate metal salt etc. can be used alone or in a combination of two or more of them. The amount varies depending on the type, and preferably is 0.001-1% by weight per gel weight.

Also, preservatives, antioxidants, plasticizers, emulsifiers, or detergents etc. can be contained if necessary.

The hydrogel sheet of the present invention is required to have such a level of adhesive power as to allow the sheet to follow a skin movement at the time of application to a wound area, and is required to have such a level of adhesive power as not to damage a regenerated skin at the time of exchange. Accordingly, the hydrogel sheet of the present invention has an adhesive power of a ball number of 8-12 in the ball tack testing method at the inclination angle of 30° carried out according to the ball tack testing method prescribed in JIS Z0237 at the time of application (before water absorption), and a ball number of 3 or less at the time of exchange (after 8-hours water absorption). If the ball number is 8-12 at the time of application, the hydrogel sheet can have an appropriate adhesive power so as to enable the sheet to follow a skin movement at the time of application to a wound area. Meanwhile, a ball number of less than 8 is not preferable because the initial adhesive power is low and the hydrogel sheet cannot follow a skin movement at the time of application to a movable wound area causing a problem of readily peeling off. Also, a ball number of greater than 12 is not preferable because the adhesive power is too strong and thus there is a risk of causing a skin irritation at the time of application to a wound area. Meanwhile, if the adhesive power is a ball number of 3 or less at the time of exchange, the hydrogel sheet does not cause a pain and does not damage a regenerated skin at the time of exchange. On the other hand, an adhesive power of a ball number of greater than 3 at the time of exchange is not preferable because the adhesive power is too strong and thus there is a risk of causing a pain and damaging a regenerated skin at the time of exchange.

As a plastic film covering the hydrogel sheet surface, polyethylene, polypropylene, polyester, or polyvinyl chloride, or films obtained by subjecting these films to a surface treatment such as silicone treatment, corona discharge treatment, roughening treatment, or plasma treatment etc. can be used.

The method for preparing the hydrogel sheet of the present invention is not especially limited, and the sheet can be prepared by a known method. For example, the hydrogel sheet can be formed by spreading the hydrogel having such constitution as mentioned above on a backing and covering the hydrogel surface with a plastic film.

If necessary, a usual sterilization method such as radiation sterilization, electron beam sterilization, or ethylene oxide sterilization etc. can be carried out.

EXAMPLES

Hereinafter, the present invention is more specifically described by showing Examples (Ex.) and Comparative Examples (Comp.), but the present invention is not limited to these Examples.

Example 1

1.6 g of carboxy vinyl polymer was dissolved into an appropriate amount of purified water, then 20 g of D-sorbitol solution was added thereto, and mixed until a homogeneous mixture was obtained. Furthermore, 0.3 g of polyacrylic acid, 1.2 g of tartaric acid, 20.7 g of concentrated glycerin, 3.5 g of carmellose sodium, 4 g of partially neutralized polyacrylate, 0.1 g of anhydrous silicic acid, 1.5 g of castor oil, 0.07 g of dihydroxyaluminum aminoacetate, 0.08 g of disodium edetate, and an appropriate amount of purified water were homogeneously mixed to prepare a hydrogel. This hydrogel was spread on urethane (20 μm)/nylon elastomer (25 g/m²) and the gel surface was covered with a polyester film to form a hydrogel sheet.

Example 2

A hydrogel was prepared by the same method as Example 1, the backing was replaced with urethane (20 μm)/nylon tricot, the hydrogel was spread on the backing, and the gel surface was covered with a polyester film to form a hydrogel sheet.

Example 3

0.5 g of anhydrous silicic acid was dissolved into an appropriate amount of purified water, then 1.0 g of urea, 0.08 g of disodium edetate, and 0.5 g of castor oil were added thereto, and mixed until a homogeneous mixture was obtained. Furthermore, 15.0 g of 20% polyacrylic acid aqueous solution, 0.3 g of tartaric acid, 16.0 g of concentrated glycerin, 4.0 g of carmellose sodium, 5.0 g of partially neutralized polyacrylate, 0.06 g of magnesium aluminometasilicate, 0.02 g of dried aluminum hydroxide gel, and an appropriate amount of purified water were homogeneously mixed to prepare a hydrogel. This hydrogel was spread on urethane (20 μm)/nylon elastomer (25 g/m²), and the gel surface was covered with a polyester film to form a hydrogel sheet.

TABLE 1

| Ingredient (% by weight) | Ex. 1 | Ex. 2 | Ex. 3 | Comp. 1 | Comp. 2 |
|---|---|---|---|---|---|
| Anhydrous silicic acid | 0.1 | 0.1 | 0.5 | 0.1 | 0.1 |
| Polyacrylic acid | 0.3 | 0.3 | — | 0.3 | 0.3 |
| Carboxy vinyl polymer | 1.6 | 1.6 | — | 1.6 | 1.6 |
| D-sorbitol solution | 20 | 20 | — | 20 | 20 |
| Concentrated glycerin | 20.7 | 20.7 | 16 | 20.7 | 20.7 |
| Carmellose sodium | 3.5 | 3.5 | 4 | 3.5 | 3.5 |
| Partially neutralized polyacrylate | 4 | 4 | 5 | 4 | 4 |
| Castor oil | 1.5 | 1.5 | 0.5 | 1.5 | 1.5 |
| 20% Polyacrylic acid aqueous solution | — | — | 15 | — | — |
| Tartaric acid | 1 | 1 | 0.3 | 1 | 1 |
| Urea | — | — | 1.0 | — | — |
| Dihydroxy-aluminum aminoacetate | 0.07 | 0.07 | — | 0.07 | 0.07 |
| Magnesium alumino-metasilicate | — | — | 0.06 | — | — |
| Dried aluminum hydroxide gel | — | — | 0.02 | — | — |
| Disodium edetate | 0.08 | 0.08 | 0.08 | 0.08 | 0.08 |
| Purified water | Appropriate amount | Appropriate amount | Appropriate amount | Appropriate amount | Appropriate amount |
| Backing | Urethane (20 μm)/Nylon elastomer (25 g/m²) | Urethane (20 μm)/Nylon tricot | Urethane (20 μm)/Nylon elastomer (25 g/m²) | PET non-woven fabric (100 g/m²) | PET (2 μm)/PET non-woven fabric (35 g/m²) |

Comparative Example 3

"DuoACTIVE ET" manufactured by ConvaTec, hydrocolloid wound covering-material

Comparative Example 4

"Opsite" manufactured by Smith & Nephew, polyurethane film wound covering-material Comparative Example 5

"VIEWGEL" manufactured by Nichiban, PVA hydrogel wound covering-material

Comparative Example 6

"Tegaderm" manufactured by 3M, hydrocolloid wound covering-material

Test Example 1

Using each of the hydrogel sheets of Examples 1-3 and the wound covering-materials obtained from Comparative Examples 1-5, stretchability, moisture permeability, water absorbability, and adhesive power were measured according to the following testing methods. Each measured value is the average value of three measurements. The results are shown in Table 2.

1) Stretchability Test

The stretchability test was carried out according to "stretch woven fabrics" in the testing method for general woven fabrics of JIS L1096.

Each test material was cut into a size of 2×6 cm to obtain a specimen and each specimen was marked at an interval of 4 cm ($L_0$). Each specimen was clipped on the outside of each mark line and placed under a constant load of 100 g, and the distance between marks was measured ($L_1$). The elongation rate was calculated by the following formula.

Elongation rate (%)=$(L_0-L_1)/L_0 \times 100$ $L_0$: Original length between marks (4 cm)
$L_1$: Length between marks under a constant load of 100 g (cm)

2) Moisture Permeability Test

The moisture permeability test was carried out by the cup method according to JIS Z0208.

About 10 mL of purified water was placed in a glass vessel (inside diameter: 56 mm, depth: 11 mm), each test material was cut into a round shape having a diameter of 80 mm (test specimen), the glass vessel opening was covered with the test specimen with the plaster surface facing inward, the brim of the glass vessel was sealed with a paraffin-based stretchable film, and the weight of the whole assemblage was measured ($W_0$).

Subsequently, the assemblage was incubated in a thermo-hygrostat at 40° C.-75% for 24 hours, allowed to cool, then the weight was precisely measured ($W_1$), and the moisture permeability was calculated by the following formula.

Moisture permeability (g/m$^2$·24 h)=$(W_0-W_1) \times 10000 \div A$ $W_0$: Weight before test (g)
$W_1$: Weight after test (g)
A: Glass vessel opening area (26.4 cm$^2$)

3) Water Absorbability Test

About 10 mL of physiological saline was placed in a stainless vessel (inside diameter: 88 mm, depth: 15 mm), each test material was cut into a size of 4×4 cm (test specimen), and stored in the vessel under a sealed condition for 8 hours with the plaster surface facing inward. The weight of the test specimen before placed in the vessel ($W_0$) and the weight of the test specimen taken out after 8 hours ($W_1$) were compared.

Absorbed amount: $W_1-W_0$

4) Adhesive Power Test

A test apparatus described in Drug Approval and Licensing Procedures in Japan 2005 (Part IV: Applications for Drug Approval and Licensing, Chapter 1: Adhesive power test) was used, and each test formulation was placed on an inclined plane forming an angle of 30 degrees with a horizontal plane, with the adhesive surface facing upward. An upper 10 cm portion and a lower 15 cm portion were covered respectively with an appropriate paper to leave 5 cm length of the adhesive surface in the middle portion.

A series of steel balls varying in diameter from 3.2 mm to 34.9 mm were allowed to roll down from the upper end of the inclined plane, and the ball number which stopped on the middle adhesive surface for 5 seconds or more was measured.

Test formulations before water absorption and test formulations after 8-hours water absorption were evaluated in this manner.

TABLE 2

|  |  | Ex. 1 | Ex. 2 | Ex. 3 | Comp. 1 | Comp. 2 | Comp. 3 | Comp. 4 | Comp. 5 |
| --- | --- | --- | --- | --- | --- | --- | --- | --- | --- |
| Elongation rate (%) | Lengthwise direction | 14.2 | 5.0 | 50 | 12.5 | 0 | 5.7 | 12.5 | 2.5 |
|  | Widthwise direction | 15.0 | 39.2 | 55 | 23.3 | 0 | 5.8 | 10.8 | 2.5 |
| Moisture permeability (g/m$^2$/24 h) |  | 884 | 1385 | 1367 | 1935 | 661 | 343 | 377 | 28 |
| Water absorption amount (g/8 h/16 cm$^2$) |  | 2.52 | 2.79 | 2.71 | 2.02 | 2.37 | 0.64 | 0 | 1.14 |
| Adhesive power (ball number) | Before water absorption | 10 | 10 | 11 | 8 | 7 | 21 | 17 | 3 |
|  | After water absorption | 2 | 2 | 3 | 3 | 1 | 2 | 8 | 1 |

Test Example 2

The moisture permeability of each backing used in Examples 1-3 and Comparative Examples 1-2 was measured by the calcium chloride method (method A-1, 40° C.-90% RH) according to JIS L1099 Testing methods for water vapor permeability of textiles. The results are shown in Table 3.

TABLE 3

|  | Ex. 1 | Ex. 2 | Ex. 3 | Comp. 1 | Comp. 2 |
| --- | --- | --- | --- | --- | --- |
| Moisture permeability (g/m$^2$/24 h) | 1282 | 3699 | 3799 | 8541 | 942 |

Test Example 3

Figure 1:
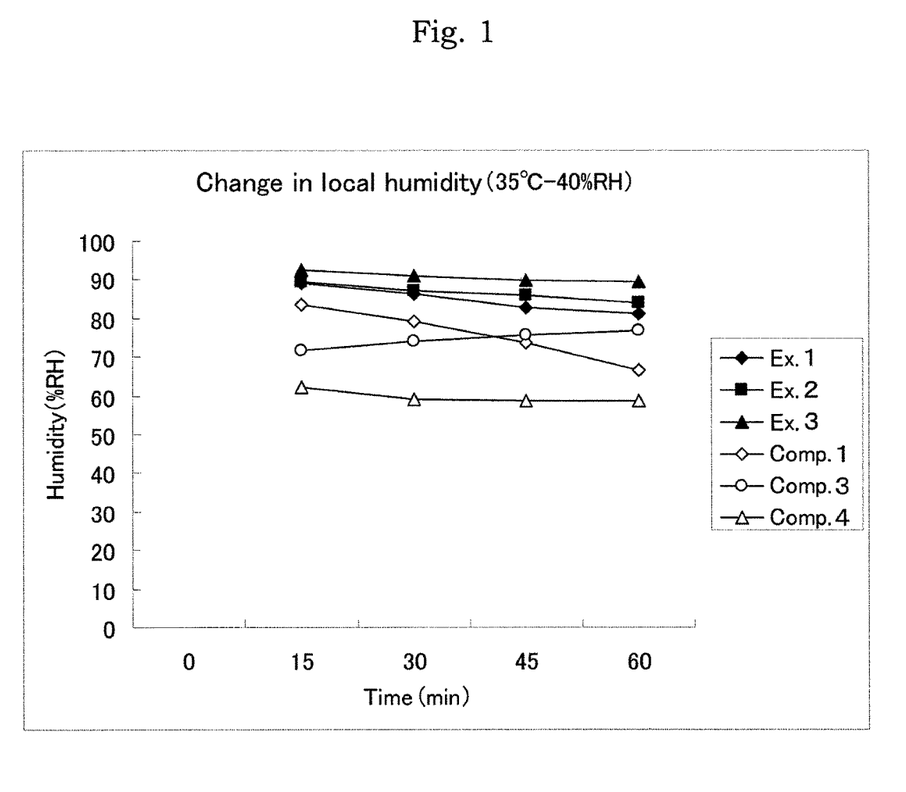
FIG. 1 shows the changes in the local humidity (1 hour).
Figure 2:
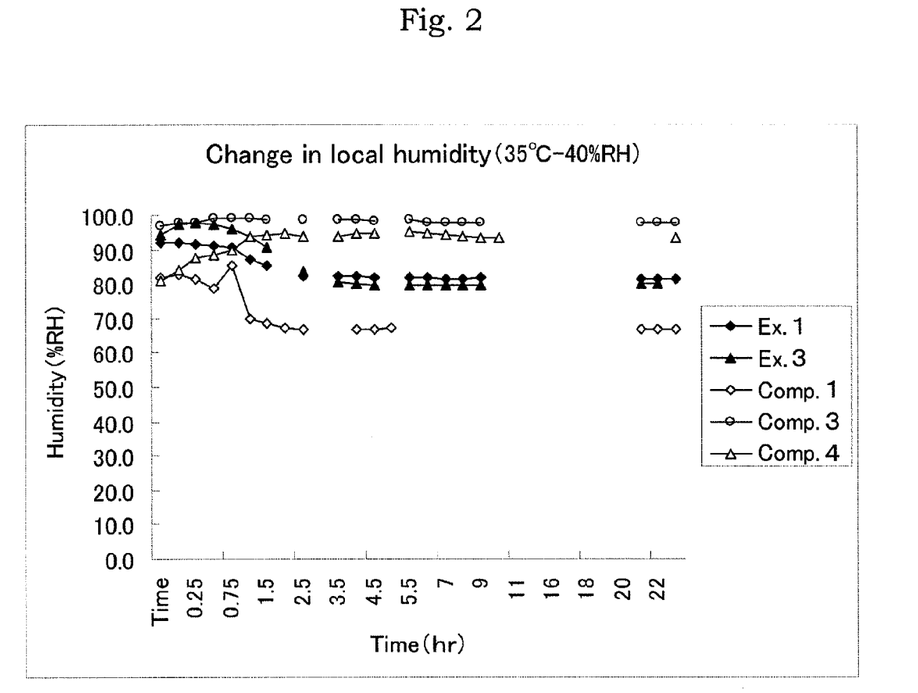
FIG. 2 shows the changes in the local humidity (24 hours).

Each of the hydrogel sheets of Examples 1-3 and each of the wound covering-materials obtained from Comparative Examples 1, 3, and 4 was applied onto a moistened sponge. The sponge was placed in a stainless vessel with warm water at 37° C. circulating therein. Furthermore, temperature-humidity sensor was inserted between the hydrogel sheet or the wound covering-material and the sponge, and the change of the temperature-humidity in application site was measured with time until 60 minutes after the start of the measurement, and subsequently until 24 hours. Each of the results is shown in FIG. 1 and FIG. 2.

Test Example 4

Each of the hydrogel sheets of Examples 1-3, and the commercially available wound covering-materials obtained from Comparative Examples 3-5 was applied onto the forearms of five volunteers for 4 hours, and evaluated for the skin adhesiveness and the pain at the time of peeling off according to the following criteria.

1) Skin Adhesiveness

The skin adhesiveness was evaluated by a three-rank system, "no peeling off", "half peeling off", and "peeling off". The results are shown in Table 4.

TABLE 4

| | Ex. 1 | Ex. 2 | Ex. 3 | Comp. 3 | Comp. 4 | Comp. 5 |
|---|---|---|---|---|---|---|
| Score | 1 | 1 | 2 | 1 | 1 | 3 |

Evaluation Criteria (Score)
1: No peeling off
2: Half peeling off
3: Peeling off 2) Pain at the Time of Peeling Off The pain at the time of peeling off from a skin was evaluated by a three-rank system, "not painful at all", "little painful", and "painful". The results are shown in Table 5.

TABLE 5

| | Ex. 1 | Ex. 2 | Ex. 3 | Comp. 3 | Comp. 4 | Comp. 5 |
|---|---|---|---|---|---|---|
| Score | 1 | 1 | 1 | 3 | 3 | 1 |

Evaluation Criteria (Score)
1: Not painful at all
2: Little painful
3: Painful

Test Example 5

The hydrogel sheet for a wound obtained from Example 2 was applied to a wounded area in which a split-thickness was deficient after the formation of a crust prepared on a rat back (n=3), peeled off after applied for 8 hours, and the state of the crust removal was evaluated by a three-rank system, "adhesion of covering-material to affected area or remaining of 75% or more of crust", "requirement of power at the time of peeling off (give a sign of pain) or remaining of 50% or more of crust", and "readily peeling off and almost no remaining of crust". As a result, the hydrogel sheet for a wound of Example 2 could be applied for 8 hours without causing a pain, and easily achieve the removal of a crust etc. from the wounded area just by peeling off the sheet. The results are shown in Table 6 below.

Evaluation Criteria (Score)
1: Readily peeling off and almost no remaining of crust
2: Requirement of power at the time of peeling off (give a sign of pain) or remaining of 50% or more of crust
3: Adhesion of covering-material to affected area or remaining of 75% or more of crust

TABLE 6

| | Example 2-1 | Example 2-2 | Example 2-3 |
|---|---|---|---|
| Score | 1 | 1 | 1 |

When the hydrogel sheet of Example 2 was applied on a dried crust for 8 hours, the crust was softened and easily peeled off together with the patch at the time of peeling off the patch.

Figure 3:
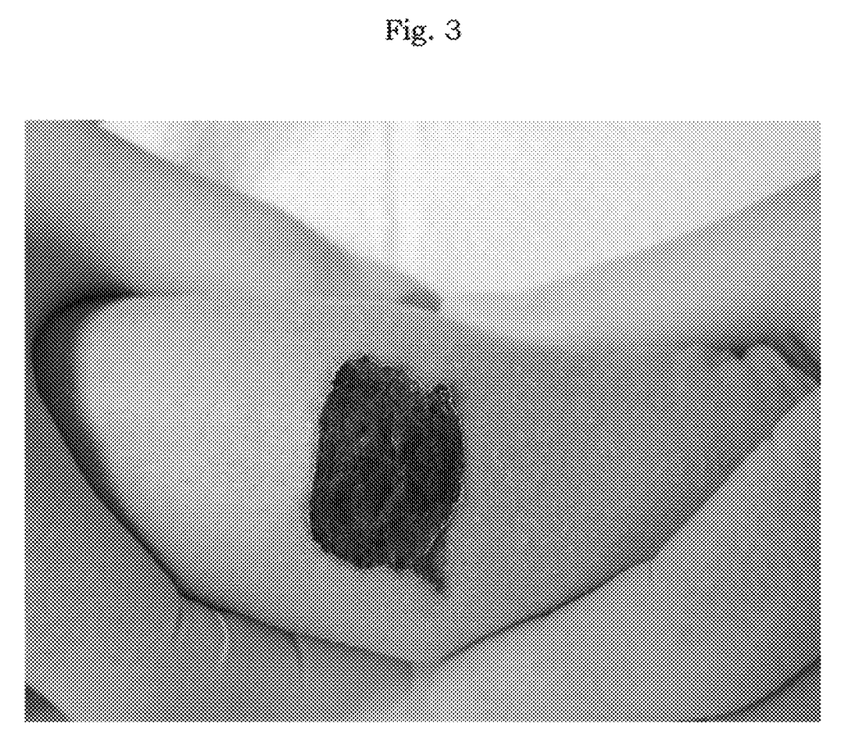
FIG. 3 shows a condition of a rat crust before the administration of a hydrogel sheet.
Figure 4:
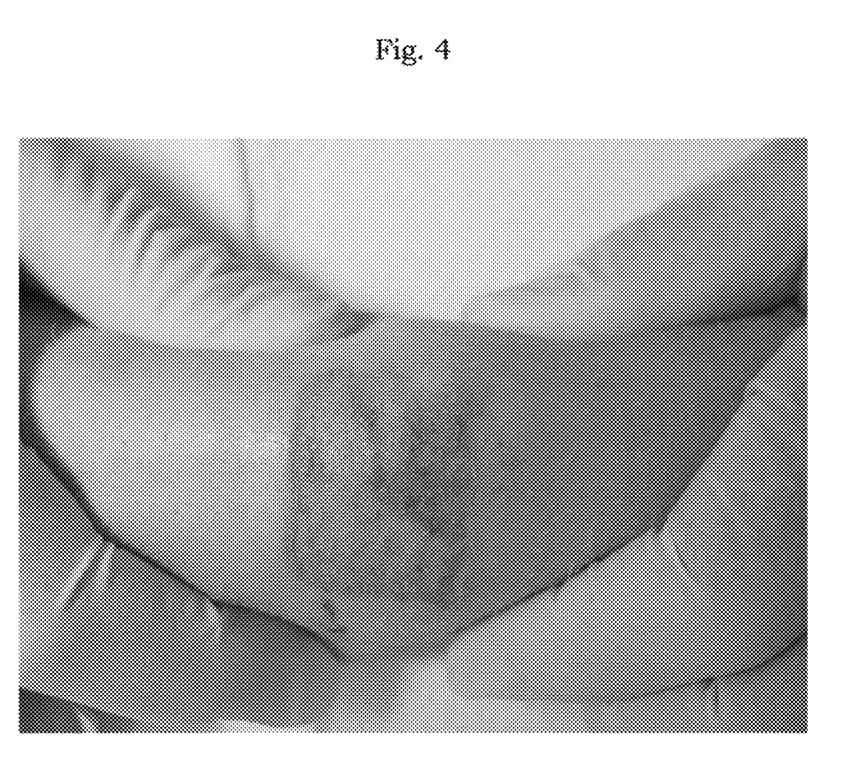
FIG. 4 shows a condition of a rat wound area after peeling off a hydrogel sheet.
Figure 5:
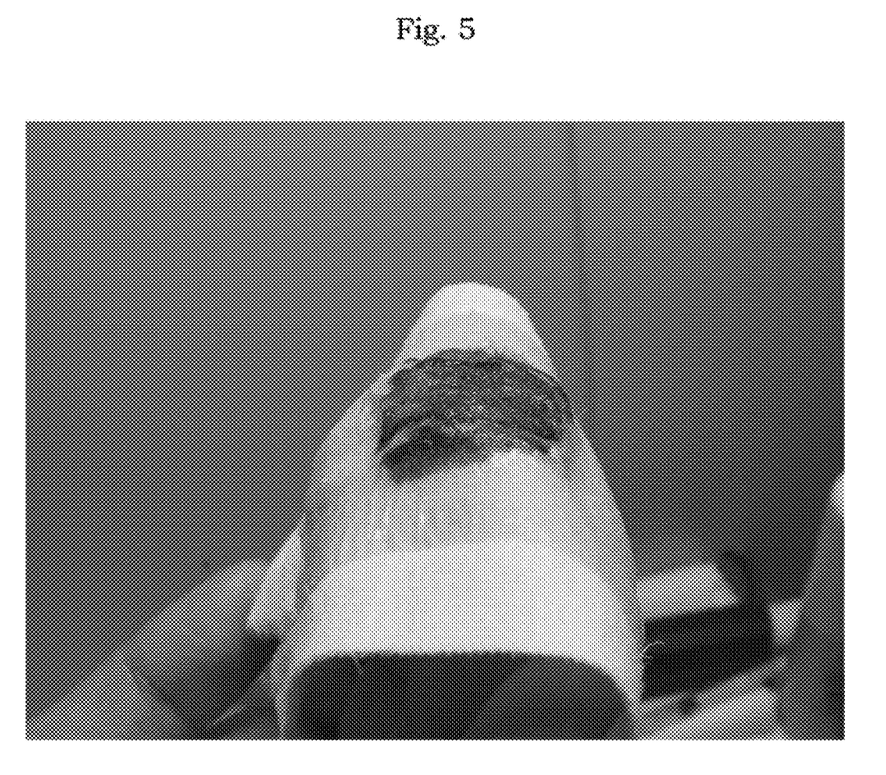
FIG. 5 shows a condition of the hydrogel sheet of Example 2 after peeling off.

The condition of the crust before administration, the condition of the wound area after peeling off and the condition of the hydrogel sheet of Example 2 after peeling off in Test Example 5 are shown in FIG. 3, FIG. 4 and FIG. 5.

Test Example 6

Each of the hydrogel sheet of Example 1 and the commercially available wound covering-material obtained from Comparative Example 6 was applied to Pseudomonas aeruginosa-infected wounds of 24 mice with exchanging the sheet or the material every 48 hours, and evaluated for the bacterial counts, the wound contraction percentages and the epithelial elongation in the tissues after 5 days of the injury. As a result, the hydrogel sheet reduced the bacterial counts in the infected wound and the marginal carrier state and maintained the moisture environment of the wounded area as well as prevented damage on a healthy skin to prevent the wound from becoming intractable. Furthermore, it was considered that the hydrogel sheet promoted a wound healing by adjusting an environment for the wound healing.

1) Bacterial Count in Tissue

A tissue in the affected area was taken, the weight was measured, and then a bacterial culture was carried out to measure the bacterial count.

Figure 6:
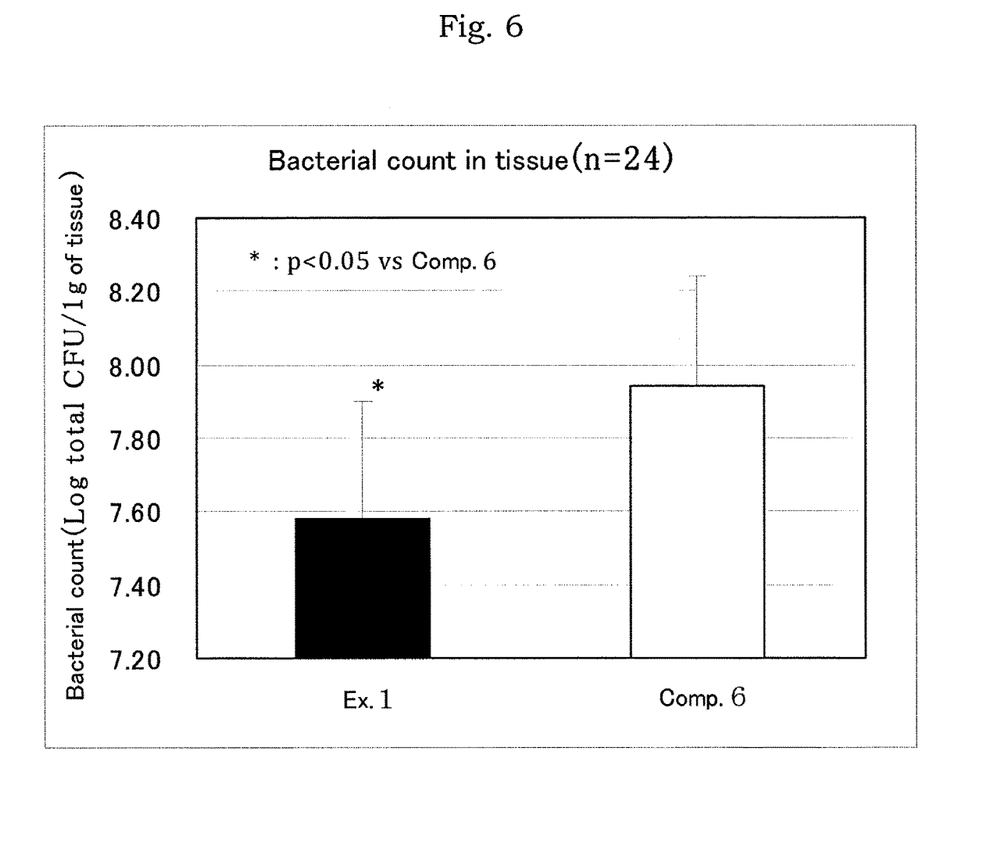
FIG. 6 shows the bacterial counts in mouse wound tissues.

As a result, as shown in FIG. 6, Example 1 significantly reduced the bacterial count compared to Comparative Example 6, and showed effectiveness against the infected wound and the wounded area in the marginal carrier state.

2) Wound Contraction Percentage

The distance of the gap between the epidermal wound margins in an affected area was measured, and the wound contraction percentage was calculated by the following formula.

Wound contraction percentage (%)=distance of gap between epidermal wound margins/distance between hair follicles in wound end×100

Figure 7:
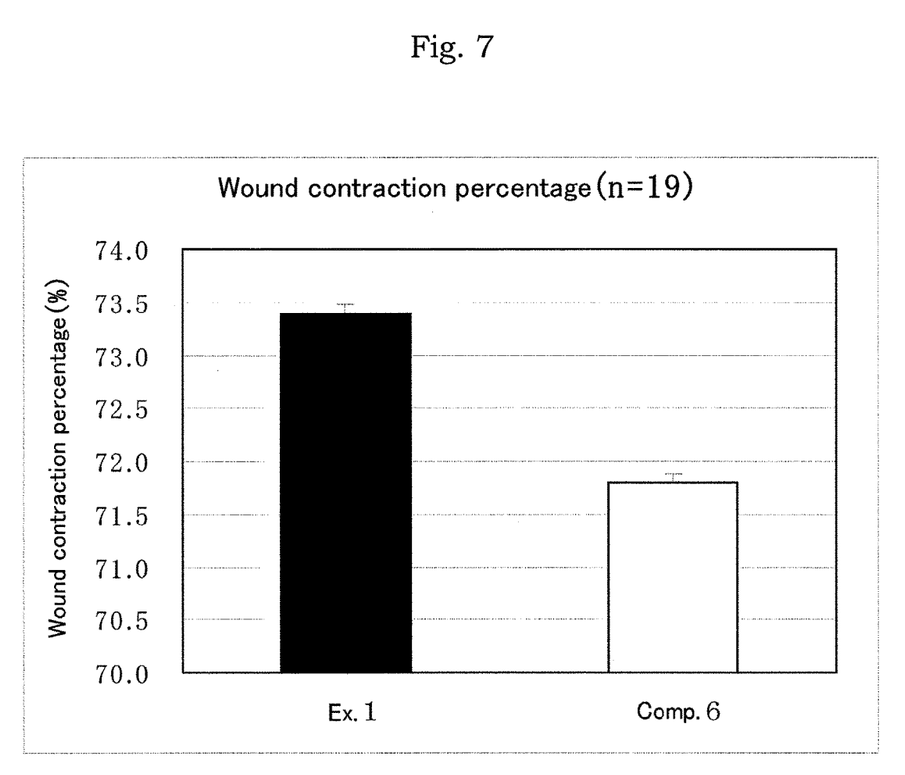
FIG. 7 shows the wound contraction percentages.

As a result, as shown in FIG. 7, Example 1 showed a greater contraction of the wound area compared to Comparative Example 6, and was considered to promote a wound healing.

3) Epithelial Elongation

The distance from a hair follicle in the wound end of the affected area to an epidermal wound margin was measured to obtain the epithelial elongation.

Figure 8:
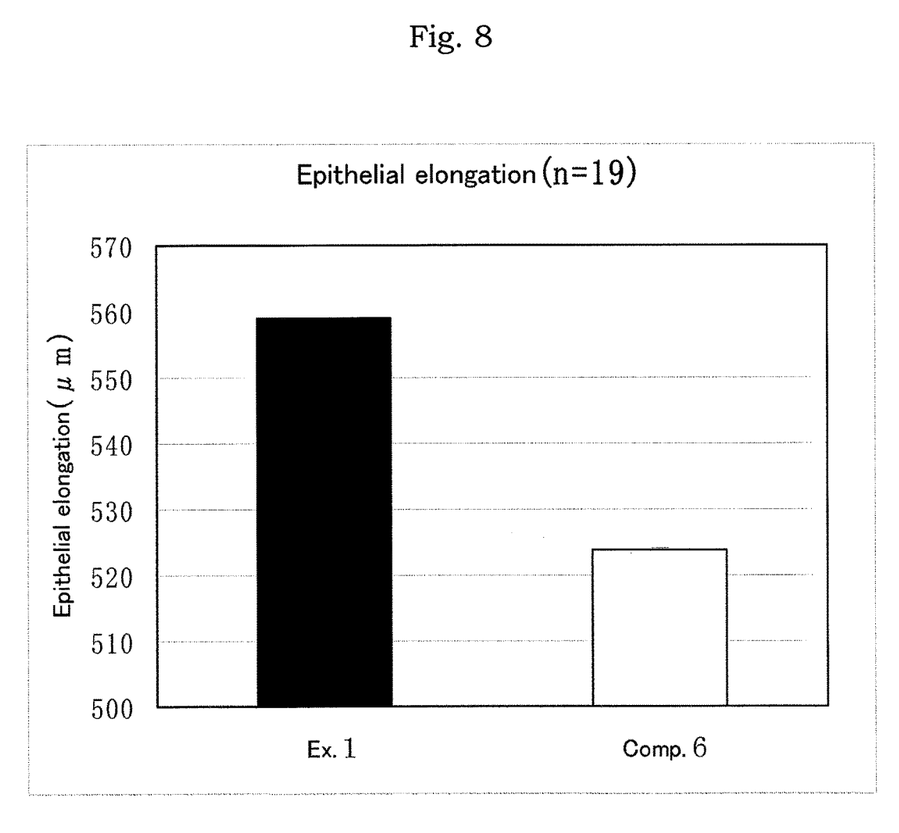
FIG. 8 shows the epithelial elongation.

As a result, as shown in FIG. 8, Example 1 showed a greater epithelial elongation compared to Comparative Example 6, and was considered to promote a wound healing.

4) Maceration Area in Surrounding Skin

On the day 3 and day 5 of the wound generation, the skin maceration area in the wound surroundings was measured.

Figure 9:
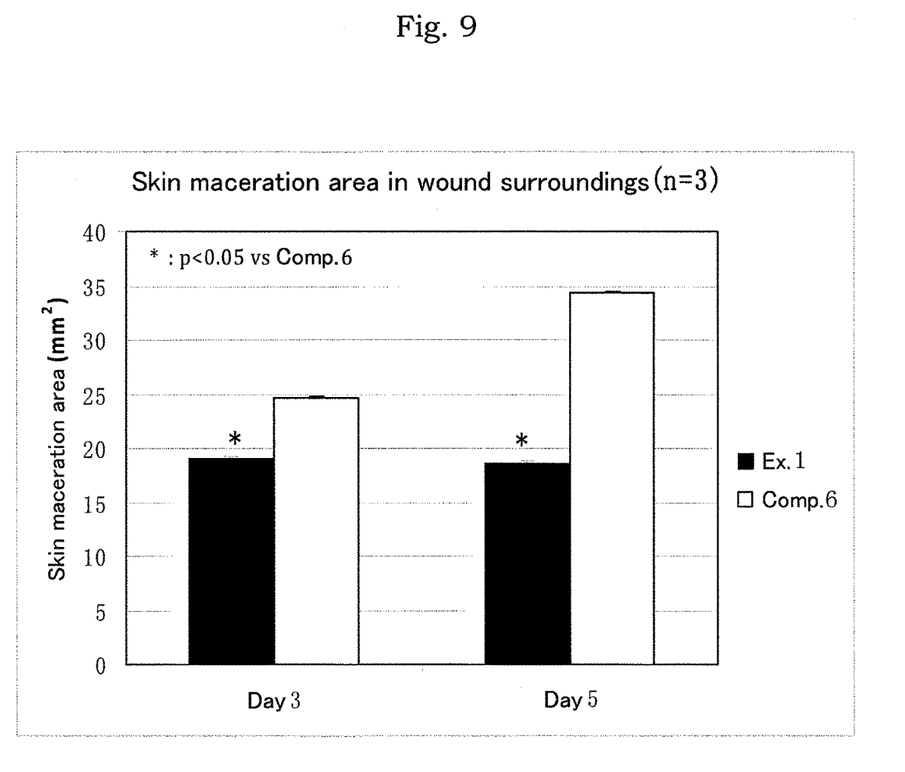
FIG. 9 shows the skin maceration areas in the wound surroundings.

As a result, as shown in FIG. 9, Comparative Example 6 developed a greater skin maceration compared to Example 1, and thus a significant difference in skin maceration area was confirmed. Furthermore, while Example 1 reduced the maceration area with time, Comparative Example 4 increased the maceration area. For this reason, it was considered that Example 1 carried out drainage of an exudate from the wound surface in a vertical direction, and thereby prevented damage due to the maceration on a healthy skin in the wound surroundings as well as reduced the risk of an infection.

INDUSTRIAL APPLICABILITY

The principal use of the hydrogel sheet for a wound of the present invention is mild removal of a crust or a necrotic tissue in a wound having a crust or a necrotic tissue etc., mild bacterial removal in a bacterial biofilm or an infected wound (antimicrobial activity), and drainage of an exudate from a wound surface in a vertical direction to maintain an appropriate moisture environment without causing a maceration of a healthy skin including the wound margin, and thereby restore the soundness of a wound bed. In this way, the hydrogel sheet for a wound of the present invention can carry out a wound management for achieving a wound healing, and is useful for a therapy of a wound having a large amount of exudates such as an infected wound, a fresh injury, a surgical wound, a burn and a bedsore.

The invention claimed is:

1. A method for carrying out wound bed preparation comprising:
    applying a hydrogel sheet to a skin wound area having a biofilm formed by bacteria in the skin wound area or having a crust in the skin wound area for at least 8 hours; and
    removing the hydrogel sheet from the skin wound area after the at least 8 hours,
        wherein the hydrogel sheet is removed after the at least 8 hours without causing pain,
        wherein the biofilm formed by bacteria in the skin wound area or the crust in the skin wound area is removed after the at least 8 hours from the skin wound area together with the hydrogel sheet;
    wherein the hydrogel sheet is prepared by spreading a hydrogel comprising a water-soluble polymer, glycerin, and water onto a two-layered laminated film,
    wherein the two-layered laminated film consists of a polyurethane film and a hydrophobic fiber,
    wherein the hydrogel sheet has a moisture permeability of 200-2000 (g/m$^2$/24 h), and
    wherein the skin wound area shows a wound contraction percentage of at least 72% after 48 hours, as measured according to the following formula:

wound contraction percentage (%)=distance of gap between epidermal wound margins/distance between hair follicles in wound end×100.

2. The method for carrying out wound bed preparation according to claim 1, wherein the water-soluble polymer is selected from the group consisting of gelatin, hydrolyzed gelatin, polyacrylic acid, sodium polyacrylate, partially neutralized polyacrylate, starch polyacrylate, polyvinyl alcohol, polyvinylpyrrolidone, hydroxypropylcellulose, hydroxypropyl methylcellulose, hydroxyethyl cellulose, methylcellulose, carmellose sodium, carboxy vinyl polymer, methoxyethylene-maleic anhydride copolymer, N-vinyl acetamide copolymer, xanthane gum, gum acacia, and mixtures thereof.

3. The method for carrying out wound bed preparation according to claim 1, wherein the water-soluble polymer is selected from the group consisting of polyacrylic acid, partially neutralized polyacrylate, carmellose sodium, and mixtures thereof.

4. The method for carrying out wound bed preparation according to claim 1, wherein the water-soluble polymer is selected from the group consisting of gelatin, hydrolyzed gelatin, starch polyacrylate, polyvinyl alcohol, polyvinylpyrrolidone, methoxyethylene-maleic anhydride copolymer, xanthane gum, gum acacia, and mixtures thereof.

5. The method for carrying out wound bed preparation according to claim 1, wherein the moisture permeability of the hydrogel sheet is 500-1500 (g/m$^2$/24 h).

6. The method for carrying out wound bed preparation according to claim 1, wherein the hydrogel sheet further comprises at least one of excipients, moisturizers, stabilizing agents, cross-linking agents, preservatives, antioxidants, plasticizers, emulsifiers, and detergents.

7. The method for carrying out wound bed preparation according to claim 1, wherein the hydrogel sheet further comprises at least one moisturizer, other than glycerin, selected from the group consisting of D-sorbitol solution, 1,3-butylene glycol, dipropylene glycol, polyethylene glycol, polypropylene glycol, and DL-sodium pyrrolidone carboxylate solution, and mixtures thereof.

8. The method for carrying out wound bed preparation according to claim 1, wherein the hydrogel sheet has an adhesive power of a ball number of 8-12 in a ball tack testing method at an inclination angle of 30° carried out according to a ball tack testing method prescribed in JIS Z0237 before water absorption, and a ball number of 3 or less after 8-hours water absorption.

9. The method for carrying out wound bed preparation according to claim 1,
    wherein the hydrogel sheet further comprises:
        an excipient that is anhydrous silicic acid;
        a moisturizer that is D-sorbitol solution;
        a stabilizing agent selected from the group consisting of tartaric acid, disodium edetate, and mixtures thereof; and
        a cross-linking agent selected from the group consisting of dihydroxy-aluminum aminoacetate, magnesium alumino-metasilicate, dried aluminum hydroxide gel, and mixture thereof; and
    wherein the water-soluble polymer is selected from the group consisting of polyacrylic acid, carboxy vinyl polymer, carmellose sodium, partially neutralized polyacrylate, and mixture thereof.

10. The method for carrying out wound bed preparation according to claim 1, wherein the skin wound area has a bacteria count of less than 7.6 Log total CFU/1 g of tissue after 48 hours.

11. The method for carrying out wound bed preparation according to claim 1 after 48 hours, wherein the skin wound area shows an epithelial elongation of 500-560 μm.

12. The method for carrying out wound bed preparation according to claim 1, wherein the skin wound area shows a skin maceration area of less than 20 mm$^2$ after 3 days and 5 days.

13. A method for carrying out wound bed preparation consisting of: applying a hydrogel sheet to a skin wound area having a biofilm formed by bacteria in the skin wound area or having a crust in the skin wound area for at least 8 hours; and removing the hydrogel sheet from the skin wound area after the at least 8 hours, wherein the hydrogel sheet is removed after the at least 8 hours without causing pain, wherein the biofilm formed by bacteria in the skin wound area or the crust in the skin wound area is removed after the at least 8 hours from the skin wound area together with the hydrogel sheet; wherein the hydrogel sheet is prepared by spreading a hydrogel comprising a water-soluble polymer, glycerin, and water onto a two-layered laminated film, wherein the two-layered laminated film consists of a polyurethane film and a hydrophobic fiber, wherein the moisture permeability of the hydrogel sheet is 200-2000 ($g/m^2/24$ h), wherein the skin wound area has a bacteria count of less than 7.6 Log total CFU/1 g of tissue after 48 hours, wherein the skin wound area shows a wound contraction percentage of at least 72% after 48 hours, as measured according to the following formula: wound contraction percentage (%)=distance of gap between epidermal wound margins/distance between hair follicles in wound end×100, wherein the skin wound area shows an epithelial elongation of 500-560 μm, and wherein the skin wound area shows a skin maceration area of less than 20 $mm^2$ after 3 days and 5 days.

14. The method for carrying out wound bed preparation according to claim 13,
wherein the hydrogel sheet further comprises:
an excipient that is anhydrous silicic acid;
a moisturizer that is D-sorbitol solution;
a stabilizing agent selected from the group consisting of tartaric acid, disodium edetate, and mixtures thereof; and
a cross-linking agent selected from the group consisting of dihydroxy-aluminum aminoacetate, magnesium alumino-metasilicate, dried aluminum hydroxide gel, and mixture thereof; and
wherein the water-soluble polymer is selected from the group consisting of polyacrylic acid, carboxy vinyl polymer, carmellose sodium, partially neutralized polyacrylate, and mixture thereof.

* * * * *